United States Patent [19]

Grimes

[11] Patent Number: 4,998,937
[45] Date of Patent: Mar. 12, 1991

[54] METHOD OF IMPLANTING EXTRAMEDULLARY FEMORAL HEAD-NECK PROSTHESIS

[76] Inventor: James B. Grimes, 1921 18th St., Bakersfield, Calif. 93301

[21] Appl. No.: 453,689

[22] Filed: Dec. 20, 1989

Related U.S. Application Data

[63] Continuation-in-part of Ser. No. 266,700, Nov. 3, 1988, abandoned.

[51] Int. Cl.$^5$ ............................. A61F 5/04; A61F 2/30
[52] U.S. Cl. ......................................... 606/89; 623/66; 623/18
[58] Field of Search .................. 606/79, 82, 83, 86, 606/87, 89, 65, 66; 623/16, 18, 22, 23, 66

[56] References Cited

U.S. PATENT DOCUMENTS

| | | | |
|---|---|---|---|
| 2,781,758 | 2/1957 | Chevalier | 623/23 |
| 2,785,673 | 3/1957 | Anderson | 623/23 |
| 4,129,903 | 12/1978 | Huggler | 623/23 |
| 4,187,559 | 2/1980 | Grell et al. | 3/1.91 |
| 4,530,114 | 6/1985 | Tepic | 623/23 |
| 4,791,919 | 12/1988 | Elloy et al. | 128/92 |

FOREIGN PATENT DOCUMENTS

| | | | |
|---|---|---|---|
| 2724234 | 12/1977 | Fed. Rep. of Germany | 623/23 |
| 3538346 | 5/1987 | Fed. Rep. of Germany | 623/23 |
| WO86/03962 | 7/1986 | PCT Int'l Appl. | 623/23 |
| 560042 | 3/1975 | Switzerland | 623/23 |
| 2166359 | 5/1986 | United Kingdom . | |

OTHER PUBLICATIONS

Howmedica, Inc., "The PCA TM Total Hip System", 1984, pp. 1–7.
Huggler et al., "The Uncemented Thrust-Plate Hip Prosthesis", The Cementless Fixation of Hip Endoprostheses, E. Morscher (ed.), 1984, Springer-Verlag, Berlin, pp. 125–132.
Schreiber et al., "First Results with the Thrust Plate Total Hip Prosthesis", pp. 130–132.
Huggler et al., "A New Approach Towards Hip-Prosthesis Design", Arch Orthop Traumat Surg., 97, (1980), pp. 141–144.

Primary Examiner—David J. Isabella
Attorney, Agent, or Firm—Senniger, Powers, Leavitt & Roedel

[57] ABSTRACT

A method for implanting an extramedullary femoral head-neck prosthesis in the femur, the latter having a shaft and a neck at the upper end of the shaft at the medial side of the femur, includes determining the axis of the medial trabecular stream, cutting the neck of the femur to form a seat on the femur neck, and drilling a bore through the shaft of the femur to extend from the neck of the femur down to the lateral side of the shaft along a line substantially parallel to the axis of the medial trabecular stream. A barrel having an open end is inserted into the bore with the open end of the barrel facing upwardly and secured in fixed position in the bore. A stem of a ball assembly is inserted coaxially into the barrel to bring a generally planar surface of the ball assembly into congruent, face-to-face engagement with the planar surface of the femur neck.

12 Claims, 6 Drawing Sheets

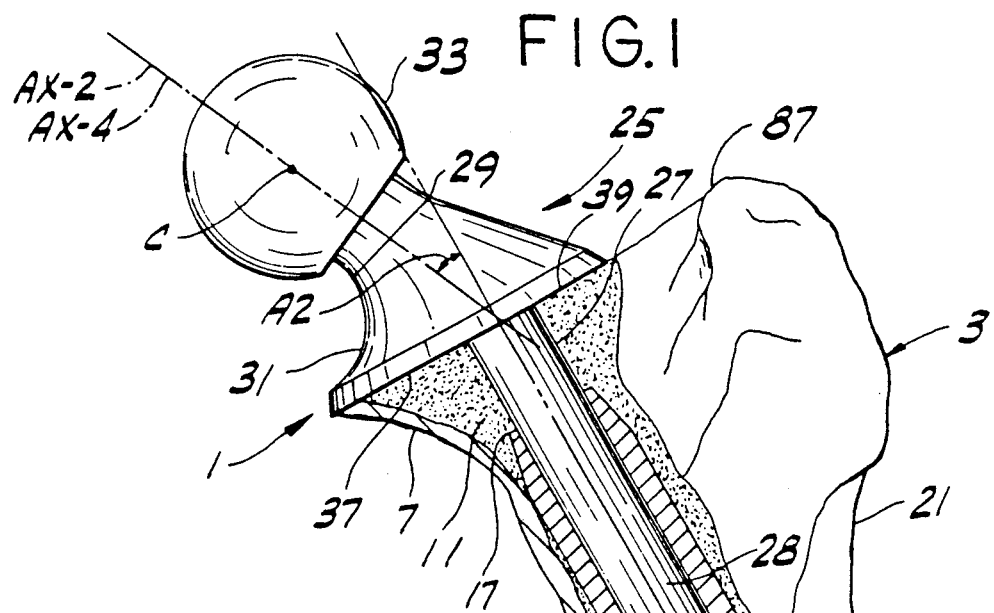
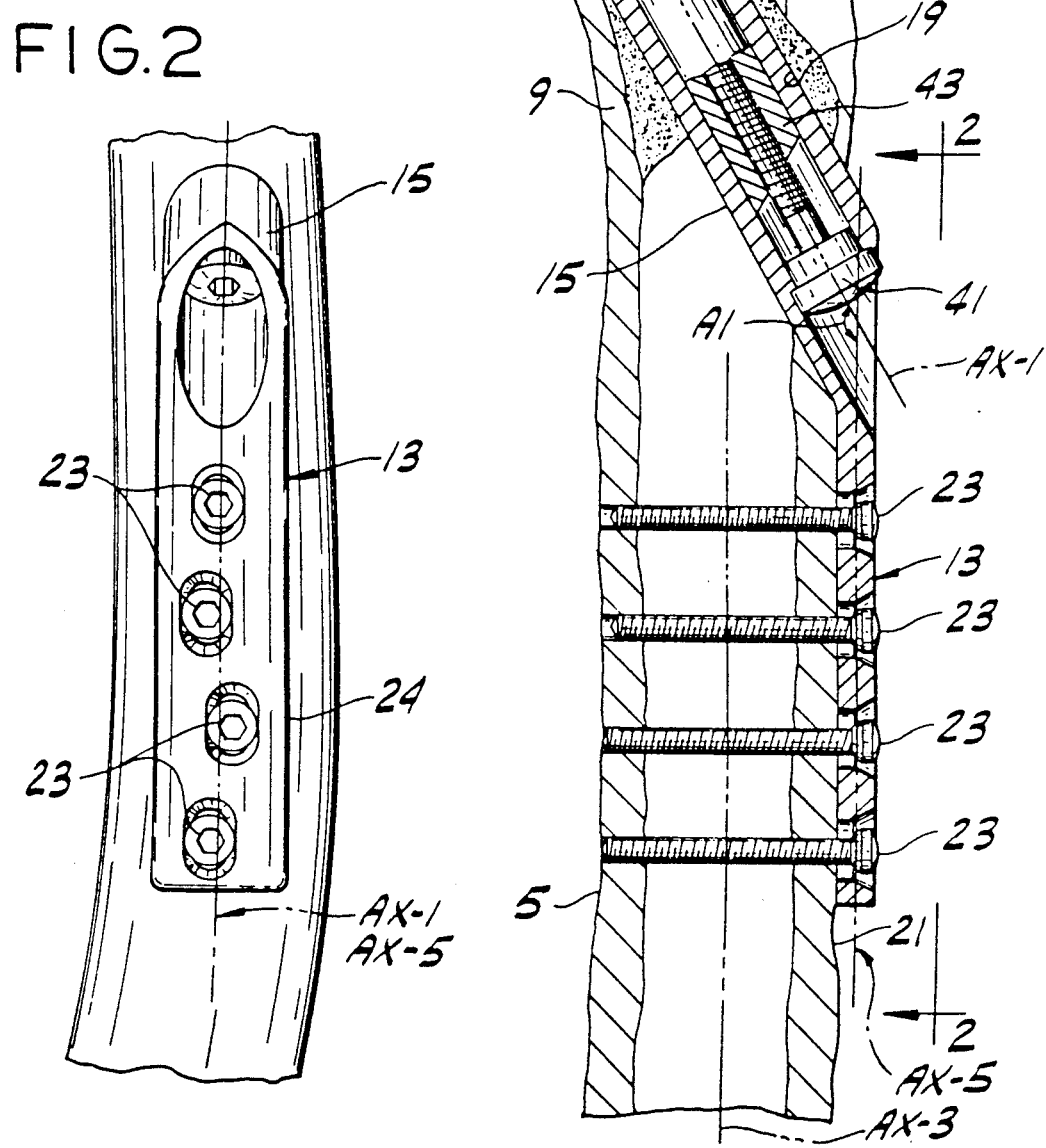

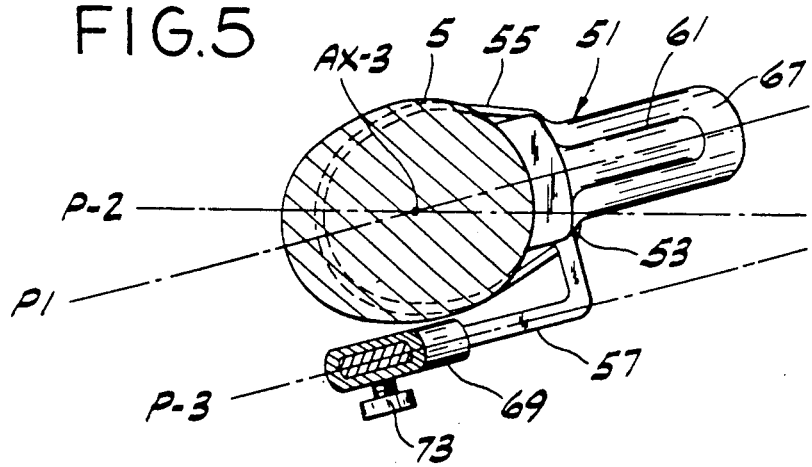
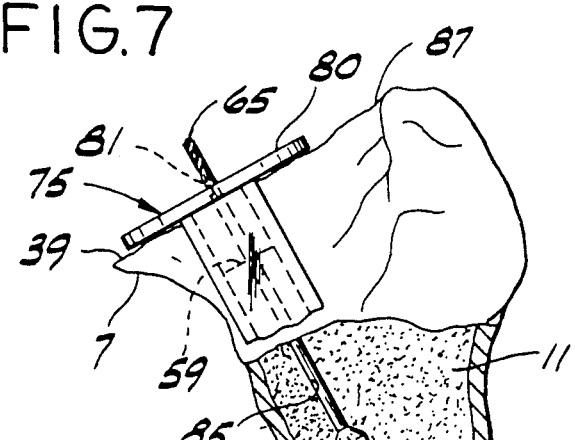
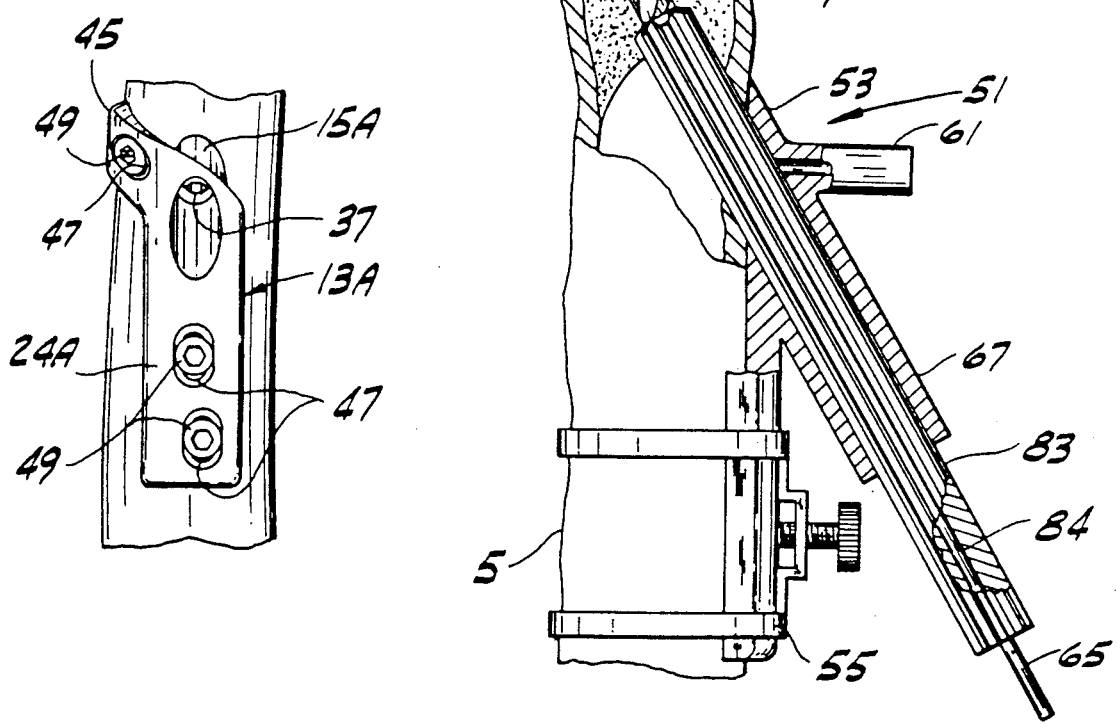

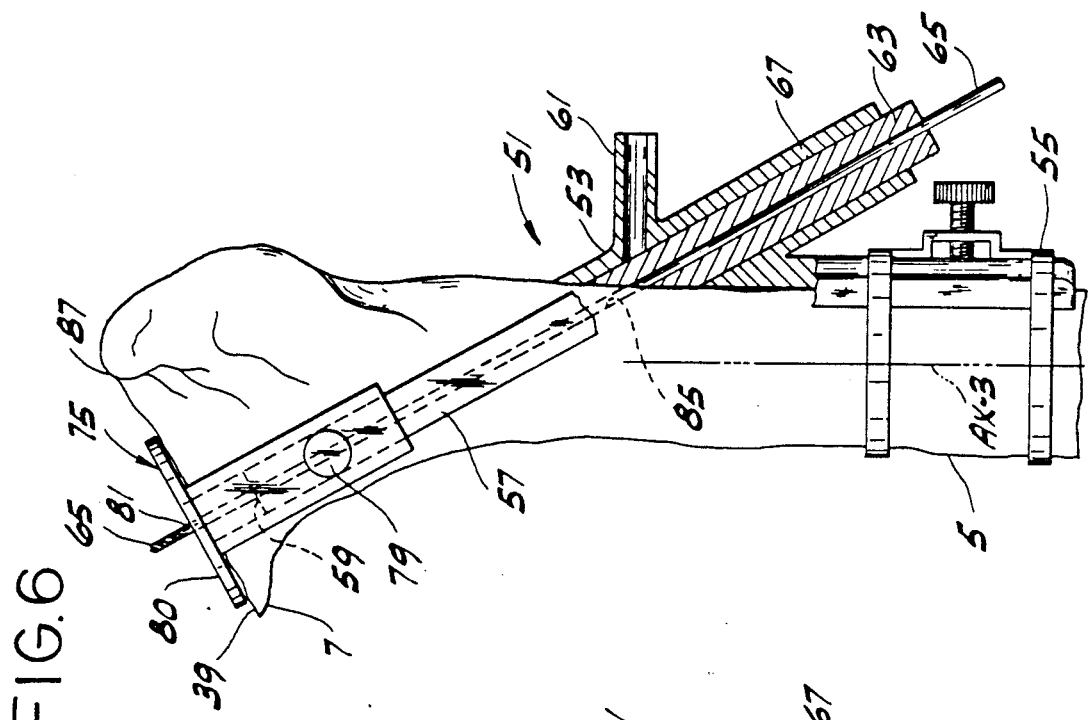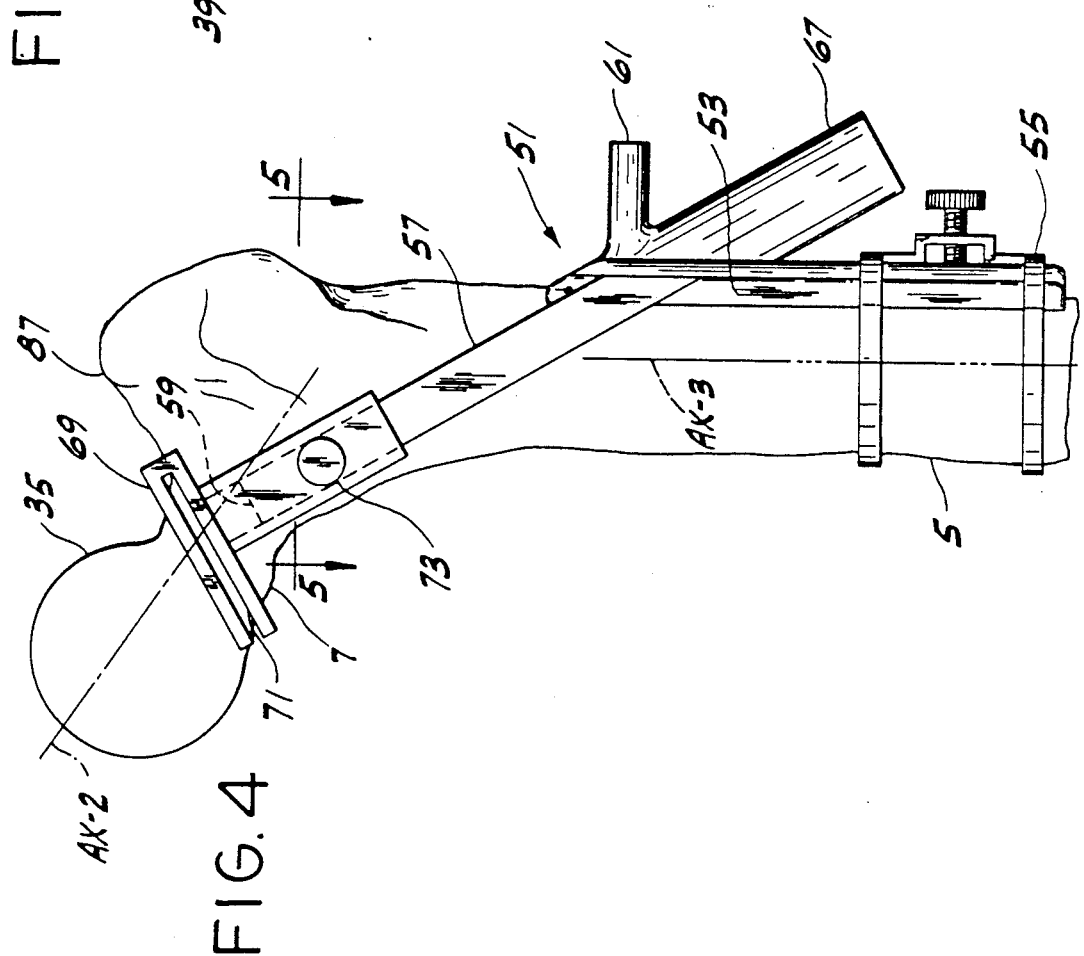

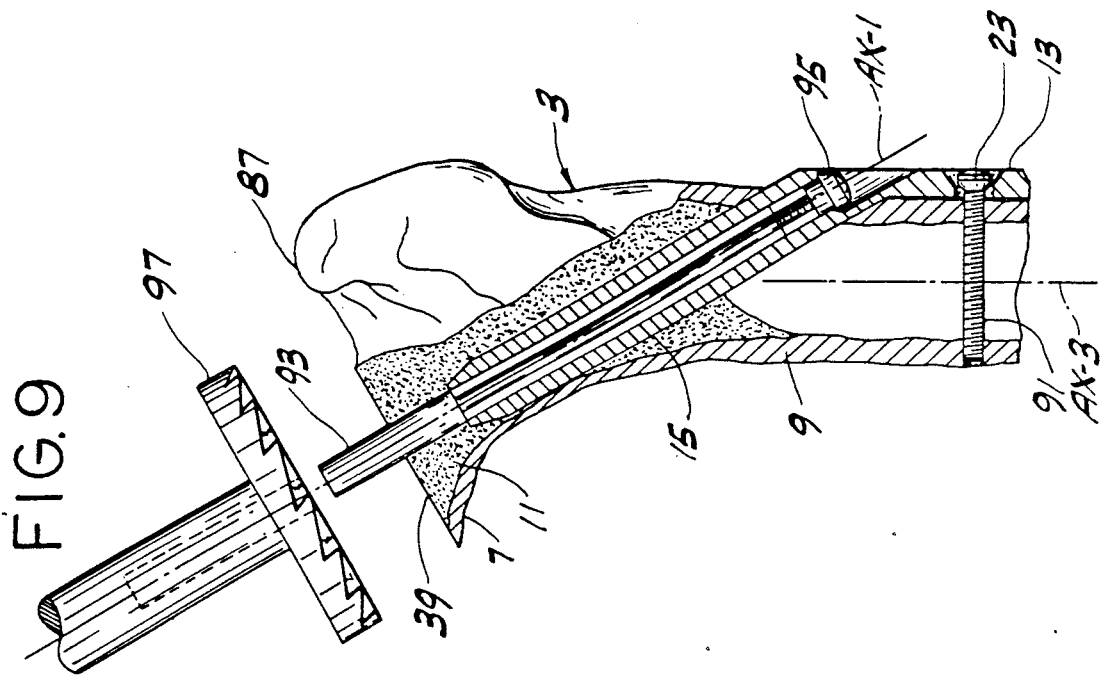
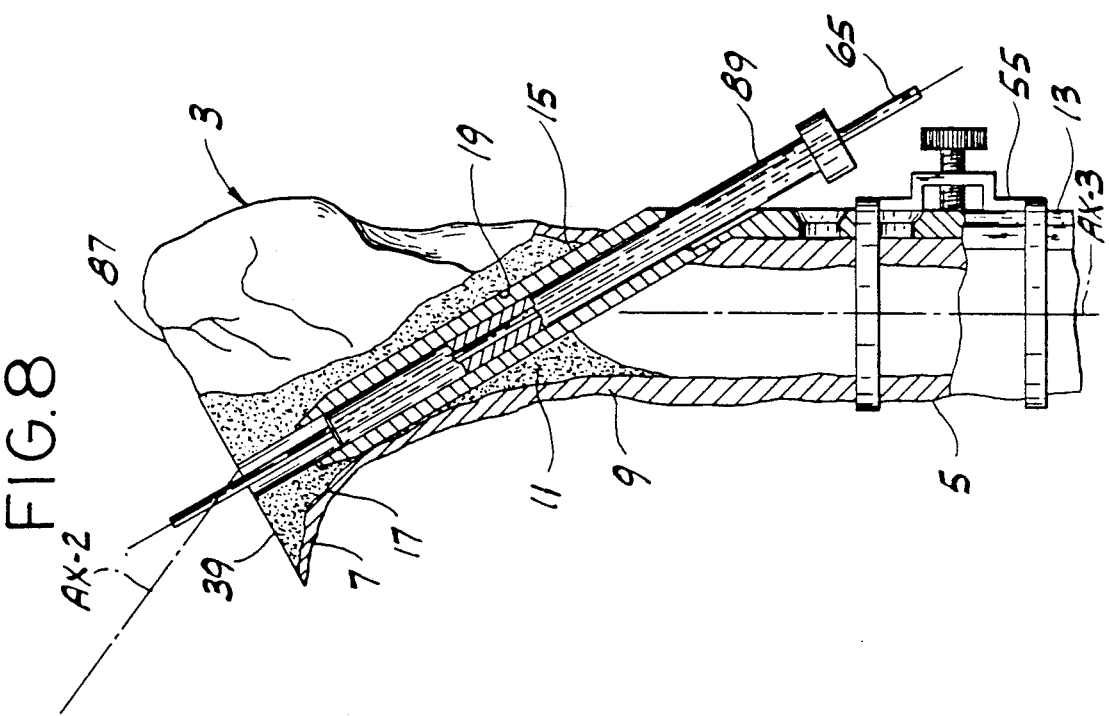

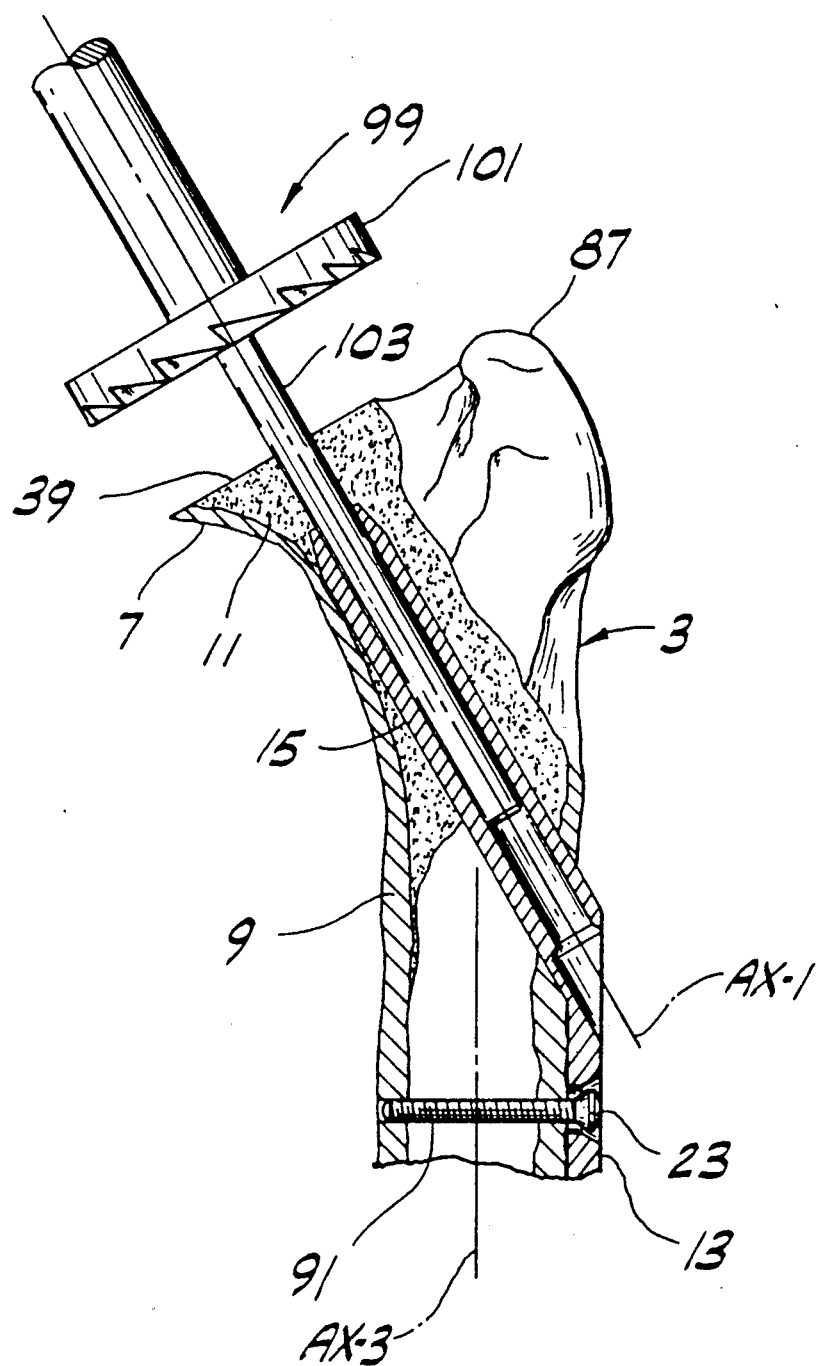

METHOD OF IMPLANTING EXTRAMEDULLARY FEMORAL HEAD-NECK PROSTHESIS

This is a continuation-in-part of application Ser. No. 07/266,700, filed Nov. 3, 1988 now abandoned.

BACKGROUND OF THE INVENTION

This invention relates generally to the art of femoral prosthetics, and more particularly to an improved method of implanting a femoral head-neck prosthesis.

Changes in the distribution of stress through a femur (thigh bone) after implanting a prosthesis may cause a number of complications, such as further deterioration of the bone. According to Wolff's law, changes in stress distribution through a bone eventually cause definite alterations in its internal structure. For example, if a portion of the femur is shielded from stresses that would normally occur, that portion is likely to deteriorate. On the other hand, where portions of the femur are subjected to greater stresses, those portions are likely to thicken in response. Of course, if the stresses are increased excessively over an extended period of time, bone cells will probably be killed ("necrosis").

Conventional "intramedullary" femoral head-neck implants, i.e., implants having a long stem secured in the medullary (marrow) canal of the femur, may cause deterioration of the femur since the proximal (upper) end of the femur is shielded from normal stress. As a result, an intramedullary prosthesis has a relatively short expected life span, at least relative to the expected life span of younger patients. Moreover, patients having intramedullary implants must reduce their activity substantially.

One approach to these problems is the "extramedullary" prosthetic joint disclosed in A. Huggler, U.S. Pat. No. 4,129,903. This prosthesis is also discussed in A. Huggler and H. Jacob, *The Uncemented Thrust-Plate Hip Prosthesis,* and A. Schreiber, H. Jacob, Y. Suezawa and A. Huggler, *First Results with the "Thrust Plate" Total Hip Prosthesis,* both in The Cementless Fixation of Hip Endoprosthesis 125–132 (E. Morscher ed. 1984) (hereinafter *Thrust-Plate Prosthesis* and *First Results,* respectively). The Huggler prosthesis includes a tension or tie rod through the bone, a pressure disc in contact with the femoral neck and a counter plate at the lateral side of the femur. One of the advantages of this kind of prosthesis is that there is sufficient supporting bone for an intramedullary implant if it becomes necessary to replace it.

There are, however, a number of undesirable side effects due to the Huggler prosthesis. For example, when the femur is loaded and unloaded as occurs during walking, the tension rod tends to move slightly with respect to the bone ("micromotion"), essentially because the modulus of elasticity of the bone and tie rod are different. As a result, the tie rod is almost constantly wearing at the bone and counter plate, possibly leading to fracture of the tie rod at its interface with the counter plate.

Huggler's approach includes positioning the thrust plate perpendicular to the longitudinal axis of the femoral neck and the tie rod along the longitudinal axis of the femoral neck (e.g., approximately 35 degrees from horizontal). According to Huggler, positioning the tie rod along the central longitudinal axis of the femoral neck is desirable to prevent motion of the tie rod relative to the bone and counter plate. More specifically, Huggler's position is that the more vertical the tie rod, the more the distal end of the tie rod will move within the counter plate (i.e., the greater the "micromotion").

However, since the tie rod of the Huggler prosthesis is aligned with the central longitudinal axis of the femoral neck, the tie rod is not aligned (or near alignment) with the generally vertical load on the femur caused by normal activity, such as walking. Thus, when the femur is loaded, the tie rod is subjected to a bending moment, which may lead to its fracture. This may have been a contributing cause to the tie rod fracture discussed in *Thrust-Plate Prosthesis,* at p. 127.

In addition, the Huggler prosthesis is anchored relatively high (proximal) on the lateral side of the femoral shaft where the cortical bone is relatively thin. This may be the reason that one-third of the patients treated with the prosthesis complained of pain in the first 6–8 months (*Final Results,* at p. 130), the pain apparently abating when the cortical bone has thickened sufficiently according to Wolff's law. Another cause of this pain may be the combination of the high position of the counter plate with its relatively high profile, which may cause irritation of muscles and tendons.

SUMMARY OF THE INVENTION

Among the several objects of the invention may be noted the provision of an improved method of implanting an extramedullary femoral head-neck prosthesis which loads the femur in a manner similar to the original femoral head and neck thereby minimizing deterioration of the femur; the provision of such a method which reduces complications and mistakes during installation; the provision of such a method which facilitates the proper alignment of the prosthesis; the provision of such a method which facilitates a congruent and close face-to-face engagement of the prosthesis with the resected femur neck; the provision of such a method which causes a minimum of trauma to a patient; the provision of such a method which allows installation with only a minimum of trial-and-error; and the provision of such a method which reduces the chances of undue heat build-up caused by friction, especially while cutting and drilling the femur, since excessive heat can kill bone cells.

In general, a method of this invention involves implanting an extramedullary femoral head-neck prosthesis in the femur, the latter having a shaft and a neck at the upper end of the shaft at the medial side of the femur. The method includes determining the axis of the medial trabecular stream, cutting the neck of the femur to form a seat on the femur neck, and drilling a bore through the shaft of the femur to extend from the neck of the femur down to the lateral side of the shaft along a line substantially parallel to the axis of the medial trabecular stream. A barrel having an open end is inserted into the bore with the open end of the barrel facing upwardly and secured in fixed position in the bore. A stem of a ball assembly is inserted coaxially into the barrel to bring a generally planar surface of the ball assembly into congruent, face-to-face engagement with the seat on the femur neck.

Other objects and features will be in part apparent and in part pointed out hereinafter.

BRIEF DESCRIPTION OF THE DRAWINGS

FIG. 1 is a vertical cross-sectional view through a femoral head-neck prosthesis of the present invention as installed on a femur;

FIG. 2 is a partial side elevation of the prosthesis of FIG. 1 showing a sideplate for securing the prosthesis to the femur;

FIG. 3 is a view similar to FIG. 2, showing a sideplate of another embodiment of a femoral head-neck prosthesis of the present invention;

FIG. 4 is a side view of a device used in the method of the present invention holding a saw guide for cutting of the femoral neck;

FIG. 5 is a cross-sectional view along line 5—5 of FIG. 4;

FIG. 6 is a side view of the device of FIG. 4 holding other accessories used in the method of the present invention;

FIG. 7 is a side view of the holding device of FIGS. 4-6 showing the femur being reamed;

FIG. 8 is a side view of the sideplate and barrel of the prosthesis of FIG. 1 being positioned on the femur; and FIG. 9 is a front elevation of a femur being finished according to the method of the present invention using a finishing tool and a separate trunnion;

FIG. 10 is a front elevation of a femur being finished using a finishing tool having an integral shaft in place of the separate trunnion and FIG. 11 is an X-ray of the femur showing the medial trabecular stream.

Corresponding reference characters indicate corresponding parts throughout the several views of the drawings.

DESCRIPTION OF PREFERRED EMBODIMENTS

Figure 11:
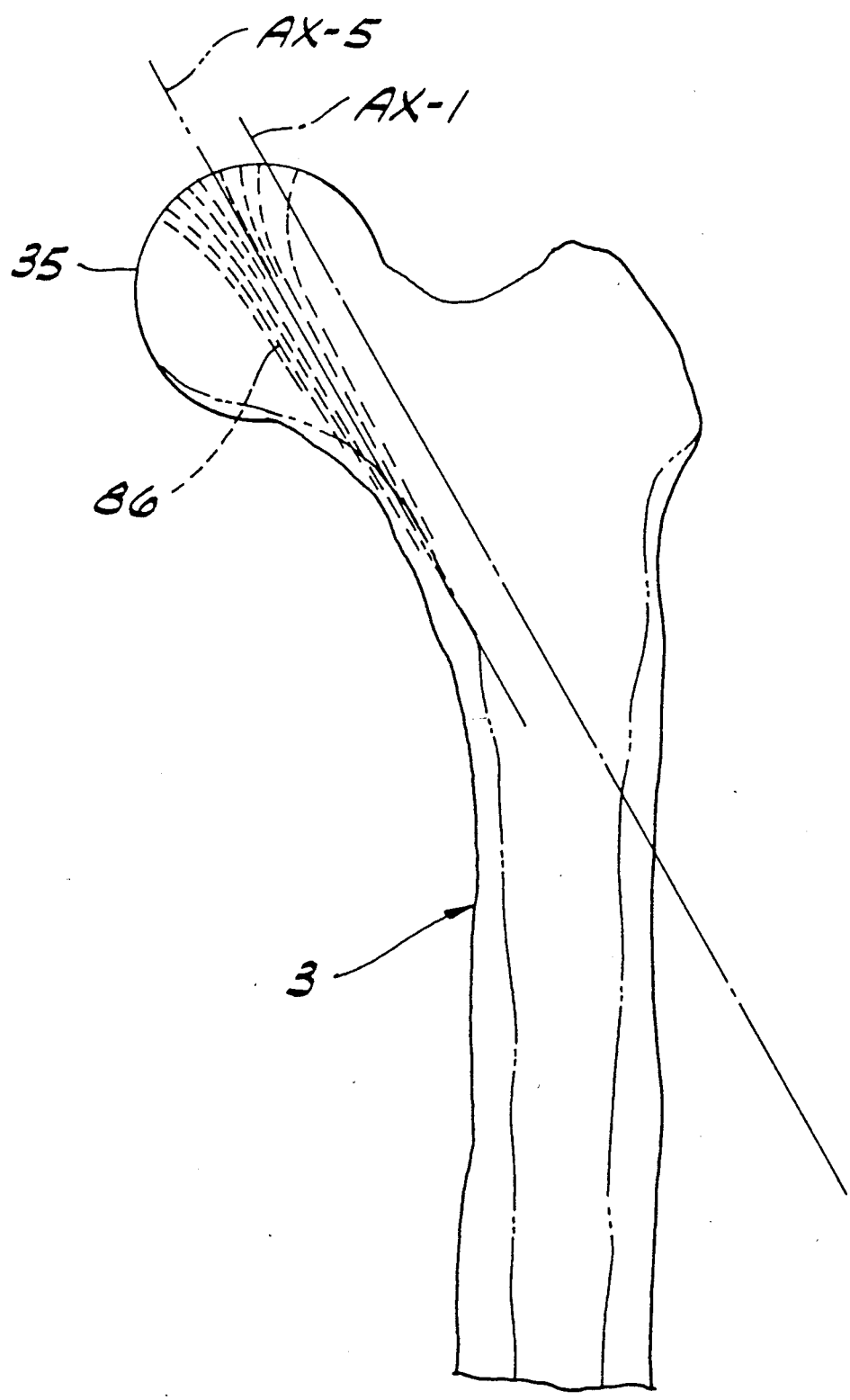

Now referring to the drawings, an extramedullary femoral head-neck prosthesis of the present invention is designated in its entirety by the reference numeral 1. The femoral head-neck prosthesis is designed for implantation in a femur generally designated 3 having a shaft 5 and a neck 7 at the upper end of the shaft at the medial side of the femur. The femur includes hard layer of cortical bone adjacent the surface of the bone and relatively soft cancellous bone 11 inside the femur.

As shown in FIG. 1, the prosthesis 1 generally comprises a sideplate 13 and a barrel 15 integral with, and extending obliquely upwardly from, the sideplate. The barrel 15 has an open upper end 17, which is inserted in a bore 19 extending obliquely upwardly through the shaft 5 of the femur from the lateral side 21 of the shaft to the neck 7 of the femur.

The central longitudinal axis AX-1 of the barrel 15 preferably is aligned with the average compression loading vector of the femur, which is the direction of the load "normally" (i.e., before implanting the prosthesis) applied to the femur. The significance of this alignment will be discussed more fully below in the context of the method of the present invention. In addition, the longitudinal axis AX-2 of the femoral neck 7 and the longitudinal axis AX-1 of bore 19 and barrel 15 lie substantially in the same vertical plane P-1 (FIG. 5) as the central longitudinal axis AX-3 of the femoral shaft so that the load on the femur is as near "normal" as possible.

As shown in FIG. 2, means is provided for securing the sideplate 13 to the femoral shaft 5 at the lateral side 21 of the femur. For example, self-tapping screws 23 through a lower portion 24 of the side plate 13 may secure the sideplate to the thick cortical bone of the femoral shaft.

The prosthesis includes a ball assembly generally designated 25 comprising a ball stem 27 adapted to be inserted coaxially into the barrel 15 through the open upper end 17 of the barrel. The ball stem 27 has a flat surface 28 for engaging a corresponding flat portion (not shown) of barrel 15 to prevent rotation of the stem within the barrel. The stem 27 is sized for a relatively close clearance fit in the barrel, the stem being slideably received in the barrel. Collar 31 at the upper end of the stem 27 engages the neck 7 of the femur face-to-face, covering substantially the entire cut surface of the femoral neck 7. A ball 33 is removably attached to a neck 29 on the collar 31, the ball and neck dimensions being selected according to the length of the femoral neck and head indicated at 7 and 35, respectively (the femoral head being shown in FIG. 4).

Preferably, the central longitudinal axis of the stem 27 of the ball assembly 25 is skewed with respect to the central longitudinal axis AX-4 of the neck 29 of the ball assembly. The ball assembly 25 is configured such that the angle between the central longitudinal axes of the ball stem 29 and ball neck 29 corresponds to the angle between the barrel axis AX-1 and the femoral shaft axis AX-3. Therefore, when the ball stem 27 is inserted in the barrel 15, the central longitudinal axis AX-4 of the ball neck 29 is approximately colinear with the axis AX-2 of the femoral neck 7.

The collar 31 of the ball assembly 25 has a downwardly facing generally planar surface 37 extending generally at right angles to the central longitudinal axis AX-1 of the ball stem 27. The surface 37 is adapted for face-to-face or congruent engagement with a seat 39 or mating surface on the femoral neck 7. The surface 37 may have metal beads thereon or be "porous coated" to allow tissue ingrowth into the interstices of surface 37. Although the seat 39 and collar surface 37 are shown as planar, other complementary shape may be used. For instance, the collar surface 37 can be conically shaped and the seat may have a complementary conically shaped depression, or the collar surface may be spherical and the seat may have a complementary spherical depression. Generally, the collar surface 37 and seat 39 will be symmetric about the barrel axis AX-1 to facilitate transmission of loads from the hip in a direction parallel to the barrel axis AX-1. Other machining operations may be added which proceed along AX-1, but do not produce a seat which is axisymmetric about AX-1.

Retainer means is provided for holding the ball stem 27 against upward movement of the stem in the barrel 15 and for pulling the ball neck 29 against the femoral neck 7 to compress or preload the femoral neck. For example, the retainer means may include a fastener 41 insertable into the lower end 43 of the ball stem 27 when the latter is inserted in the barrel 15. The head of the fastener 41 is engageable with the lower end of the barrel 15 for holding the ball stem 27 against upward movement in the barrel.

It will be observed that the fastener 41 merely holds the stem in the barrel; it does not bear the weight of the patient. The femur 3, including the femoral neck 7, bears the weight of the patient in a near normal fashion so that atrophy of the bone is prevented. Moreover, since the ball stem 27 is slideably received in the barrel 15, friction or wear caused by motion of the stem relative to the barrel or bone would be between the stem and barrel. The bone is thus protected by the barrel 15. It will, therefore, be observed that, unlike conventional implants, "micromotion" is accommodated by the prosthesis of the present invention. Small amplitude movements of the stem in the barrel, such as are caused by cyclical loading experienced during normal walking, are guided by the barrel in a direction generally parallel to the average compression loading vector of the hip (i.e., "normal" loading). Therefore, the femur experiences near normal stress despite the occurrence of micromotion.

FIG. 3 illustrates another embodiment of the invention generally corresponding to the embodiment of FIGS. 1 and 2, the principal difference being that the sideplate, here designated 13A, has an upper portion 45 above the juncture of the barrel 15A and the sideplate in addition to a lower portion 24A below the juncture of the barrel and the sideplate. The upper and lower portions 45 and 24A, respectively, of the sideplate 13A have holes 47 therethrough for receiving fasteners (e.g., self-tapping screws 49) to secure the sideplate to the femur shaft 5.

While a number of different devices may be helpful for implanting the femoral head-neck prosthesis, a special device generally designated 51 and shown in FIGS. 4–7 is particularly adapted to be removably secured to the femoral shaft for holding a plurality of cutting, drilling and reaming accessories in position with respect to the femur.

As shown in FIG. 4, the holding device 51 comprises a body 53 adapted to be removably secured (e.g., by clamp 55) in face-to-face engagement with the femoral shaft 5, and an arm or outrigger portion 57 extending at an angle upwardly and outwardly from the body at one side of the femoral shaft 5. The upper end 59 of the arm is adapted to be centered with respect to the base of the femoral neck 7. The body 53 and the arm 57 are configured such that the arm extends from the body along a line substantially parallel to the average compression loading vector (the "normal" direction in which the femur is loaded) for the femur of the specific patient when the body is attached to the femur.

As shown in FIG. 6, the body 53 of the holding device 51 includes a tubular guide member 61 having a bore therethrough for a starter drill (not shown). The tubular guide member 61 is adapted to be at an angle of approximately 90 degrees with respect to the central longitudinal axis AX-3 of the femur shaft 7 when the holding device is clamped thereto.

Preferably, holding device 51 includes a guide sleeve 63 for guiding a drill-tipped guide pin 65 into the femoral shaft 5 at an angle of approximately equal to the angle of the average compression loading vector. The sleeve 63 is preferably adapted to be slideably received in a guide barrel 67 formed as an integral part of the body 53 of device 51. The sleeve 63 is separately removable from the guide barrel 67 so that after the guide pin 65 has passed through the femoral neck 7, the sleeve may be removed while the guide pin remains in position.

As noted above, device 51 is adapted for holding a variety of different accessories used in implanting the prosthesis 1 of the present invention. One such accessory is a saw guide 69 adapted to be detachably mounted at the upper end 59 of the arm 57 for guiding a saw blade to cut the femoral neck 7 to form surface 39. As shown in FIG. 4, the saw guide 69 has a sawcut slot 71 generally perpendicular to the central longitudinal axis of arm 57, the arrangement being such that when the holding device 51 is secured in the position shown, the slot is at an angle generally perpendicular to the average compression loading vector of the femur. It is contemplated that the slot 71 will also be generally perpendicular to the central longitudinal axis of the arm 57. The saw guide 69 is slideably adjustable along the arm 57 to properly position it with respect to the femoral neck 7. A set screw 73 is provided for securing the saw guide in adjusted position.

Indicated generally at 75 is another accessory for checking the position of the holding device 51 with respect to the femur 3. Accessory 75 is slideably adjustable along arm 57 to properly position it with respect to the femoral neck seat 39 of the femoral neck. The accessory is not rotatable with respect to the arm 57. A set screw 79 is provided for detachably securing the accessory 75 in adjusted position. Accessory 75 comprises a relatively thin flat member 80 extending laterally outwardly to a position in which it is disposed in a plane generally parallel to and immediately above the seat 39. Member 80 has an opening 81 in alignment with the central longitudinal axis of the guide sleeve 63. Thus, opening 81 is adapted for indicating the location on the cut surface 39 of the femoral neck where the guide pin will come through so that the position of the holding device 51 may be checked for accuracy prior to drilling. It will be noted that arm 57 of the holding device 51 is substantially parallel to the central longitudinal axis of the guide sleeve and barrel 63 and 67, respectively, so that the sleeve and barrel axis is aligned with the opening 81 regardless of the position of the accessory 75 along the arm.

A cannulated reamer 83 (FIG. 7) is sized to be slideably received in the barrel 67. A central axial bore 84 through the reamer 83 is sized to slideably receive the guide pin 65 therein. It will be observed that the reamer 83 is adapted to slide into the guide barrel 67 over the guide pin 65 so that the guide pin and barrel guide the reamer as it reams the bore 85 created by the guide pin. The reamer 83 may rotate around a stationary guide pin 65, or the reamer and the guide pin may rotate together. It will be observed that during the reaming process, the guide pin 65 projects through the opening 81 in member 80. This serves to stabilize the guide pin 65 while the femur is being reamed.

The method of the present invention for implanting the prosthesis 1 assures close replication of normal loading of the femur (i.e., loading prior to implantation of the prosthesis). A femur head-neck prosthesis which fails to replicate normal loading conditions will change the stress distribution through the femur. As mentioned above, according to Wolff's law these changes in stress distribution eventually cause alterations in the internal structure of the bone. Those portions subject to a lesser stress than before are likely to deteriorate and those subject to greater stress than before are likely to thicken. Excessive increases in stress over those associated with normal loading may kill the bone cells if the stress is applied over an extended period of time. To replicate normal loading, the method of the present invention aligns the stem 27 of the prosthesis 1 with the average compression loading vector for the particular femur, which vector is variable from person to person.

The human femur has two externally visible axes: the axis of the femoral neck AX-4 and the axis of the femoral shaft AX-3. However, the bone is not loaded along either of these two visible axes, but rather is loaded through a third axis (parallel to the average compression loading vector) which is not externally apparent. In response to compressive loading and the strain energy density experienced by the femur, reinforcing lines of bone, which are called compression trabeculae, form within the femur. The collection of these reinforcing lines is the compression trabecular stream. The particular collection of compression trabeculae in the femur neck, as shown in FIG. 11, is referred to as the medial trabecular stream 86, and the average direction of the medial trabecular stream may be referred to as the medial trabecular stream axis AX-5. The angle of this axis AX-5 to the central longitudinal axis of the femur shaft AX-3 generally ranges from 140 to 170 degrees.

To install the prosthesis 1 in the femur in accordance with the method of this invention, the medial trabecular stream axis AX-5 is determined by taking an X-ray of the femur (FIG. 11) and establishing the average direction of the medial trabecular stream 86. It is to be understood that the medial trabecular stream axis may be determined by other forms of radiological examination. The holding device 51 is configured so that when the body 53 is attached to the femoral shaft, the arm 57 will extend from the body along a line substantially parallel to the medial trabecular stream axis AX-5, and the central longitudinal axis of the guide barrel 67 of the holding device will be substantially parallel to the medial trabecular stream axis. Similarly, the barrel 15 and sideplate are configured so that when the sideplate is attached to the femoral shaft, the barrel extends from the sideplate along a line substantially parallel to the medial trabecular stream axis AX-5. The ball assembly 25 is also configured such that the angle between the central longitudinal axes of the ball stem 27 and the ball neck 29 is such that when the ball stem is inserted into the barrel 15, the central longitudinal axis of the ball neck AX-4 is colinear with the central longitudinal axis AX-2 of the femoral neck.

The hip joint and the lateral (i.e., right in the drawings) side of the femur are then surgically exposed. A vertical plane P-1 through the central longitudinal axis AX-2 of the femoral neck 7 is typically at an angle of approximately 15 degrees anterior to a lateralmedial plane P-2 through the central longitudinal axis AX-3 of the femoral shaft 5, as shown in FIG. 5. This angle is commonly referred to as the "anteversion" of the femoral neck 7. Accordingly, the device 51 is positioned radially on the femur such that the vertical axis of body 53 lies in plane P-1 approximately 15 degrees posterior from the lateralmedial plane P-2 (since the body is lateral of axis AX-3 and the femoral neck 7 is medial). In this position, a vertical plane P-3 through arm 57 should be parallel to plane P-1. In addition, the holding device 51 is positioned proximally-distally on the femur such that the upper end 59 of arm 57 is centered with respect to the base of the femoral neck 7, as shown in FIG. 4. The device 51 is then clamped on the femoral shaft 5 by clamp 55. The saw guide 69 is positioned (proximally-distally) on arm 57 such that the slot 71 is located adjacent the base of the femoral neck 7 and generally aligned with the upper surface of the lateral femoral cortex 87 of the femur, as shown in FIG. 4. In this position, the slot 71 should be at an angle approximately perpendicular to the medial trabecular stream axis AX-5. Then set screw 73 is tightened to firmly attach the saw guide 69 to the arm 57.

With the saw guide 69 in place, the neck 7 is cut with an oscillating saw (not shown) by passing the saw through the slot 71 to form the seat 39 extending from the lateral femoral cortex 87 at an angle of perpendicular to the barrel-stem axis AX-1 and to the medial trabecular stream axis AX-5. The saw guide 69 is then removed from the arm 57, leaving the device 51 attached to the femoral shaft in its original position, and the femoral head 35 is removed.

If a total hip replacement (i.e., replacement of the femoral head 35 and acetabulum (not shown)) is required, the acetabulum should now be prepared.

As shown in FIGS. 6 and 7, the opening 81 in member 80 of accessory 75 is centered with respect to the seat 39 and secured to the arm 57. Some adjustment of the holding device 51 may be necessary to center opening 81 with respect to the seat 39 of the femoral neck. This may be accomplished by loosening the clamp 55 and adjusting the body 57 of the device 51. For example, if opening 81 is too medial (i.e., leftward in the drawings), the holding device 51 should be positioned more proximal on the femoral shaft 5 (upward in the drawings), and if the opening is too lateral (rightward in the drawings), the pin should be positioned more distal on the femoral shaft. In addition, if the opening 81 is anterior or posterior to the center of seat 39, the "anteversion" may be adjusted by slightly turning the device 51 on the femoral shaft 5.

With the opening 81 centered, a drill (not shown) is inserted through the tubular guide member 61 to make a relatively short starter hole (also not shown) in the lateral femoral cortex. Without a starter hole, the guide pin 65 might tend to travel or "walk" along the lateral femoral cortex due to the acute angle of entry, or be deflected from its correct angle (e.g., parallel to the medial trabecular stream axis) through the femur. The guide sleeve 63 should now be inserted in the guide barrel 67 of the holding device 51.

The drill-tipped guide pin 65 is then inserted into the guide barrel 67, and a bore 85 is drilled up through the lateral femoral cortex and through the seat 39 on the femoral neck 7. The bore 85 extends obliquely from the neck 7 of the femur down to the lateral side of the shaft along a line substantially parallel to the medial trabecular stream axis AX-5. The guide pin 65 should exit the seat 39 on the femoral neck 7 through the opening 81 of accessory 75.

If the guide pin 65 is significantly (e.g., more than 5 mm) off center, the holding device 51 should be adjusted. For example, if the pin 65 is too medial (i.e., leftward in the drawings), the device 51 should be positioned more proximal on the femoral shaft 5 (upward in the drawings), and if the pin is too lateral (rightward in the drawings), the pin should be positioned more distal on the femoral shaft. In addition, if the pin 65 extends through the seat 39 anterior or posterior of the opening 81 of accessory 75, the "anteversion" may be adjusted by slightly turning the device 51 on the femoral shaft 5. It should, however, be noted that device 51 will reduce or eliminate the trial-and-error process discussed in this paragraph.

When the guide pin 65 is in the right position, the guide sleeve 63 is removed from the guide barrel, and the guide pin and accessory 75 are left in place. As noted above, accessory 75 stabilizes the proximal end of the guide pin 65.

As shown in FIG. 7, the cannulated reamer 83 is then inserted in the guide barrel 67 over the guide pin 65 to form bore 19 through the lateral femoral cortex along a line substantially parallel to the medial trabecular stream axis AX-5. Since the body 53 of the holding device is anteverted approximately 15 degrees with respect to the femur, the bore 19 lies in plane P-1 (and is approximately 15 degrees anteriorly oriented with respect to the transverse axis of the knee, which is parallel to lateral-medial plane P-2). The holding device 51 is then removed from the femur.

In the next step of the process, the barrel 15 of the prosthesis 1 is inserted into the bore 19 with the open end 17 of the barrel facing upwardly. A pin sleeve 89 (FIG. 8) is inserted into the barrel 15, and the guide pin 65 is inserted into the sleeve to recheck the position of the bore 19 with respect to the center of the seat 39 of the femoral neck. The radial orientation or "anteversion" of bore 19 is also checked. The longitudinal axis AX-2 of the femoral neck 7 and the axis AX-1 of bore 19 should lie in the same vertical plane P-1 as the central longitudinal axis AX-3 of the femoral shaft. This plane is at an angle of approximately 15 degrees with respect to the transverse axis (not shown) of the knees, which is parallel to plane P-2.

If the position of the prosthesis 1 is satisfactory, the sideplate 13 is clamped in place, and the pin sleeve 89 and guide pin 65 are removed. Holes 91 are then drilled through the screw holes in the sideplate 13, and self-tapping screws 23 of appropriate length are inserted through the sideplate to fasten it to the femoral shaft 5, thereby securing the barrel 15 in fixed position in the bore 19 such that the axis of the barrel is thereafter rigidly defined.

The upper end of the barrel 15 is checked to determine whether it is in contact with the hard cortical bone 9. Contact of the barrel with the hard cortical bone 9 causes loads directed laterally of the barrel axis AX-1 to be supported not only by the collar 31, but also by the barrel. This contact distributes the load over a greater area of the bone, and is believed to reduce the stress experienced by the femur at its upper end to near normal levels. Should the upper end of the barrel 15 not contact the cortical bone 9, then a sleeve (not shown) may be placed in the bore around the upper end of the barrel. The sleeve is appropriately dimensioned so that it contacts the hard cortical bone 9.

After the sideplate 13 and barrel 15 are secured to the femur and the position of the upper end of the barrel is checked, a planing trunnion 93 is inserted into and suitably secured to the barrel against rotational and axial movement relative to the barrel so that it projects upwardly from the seat 39 of the femoral neck 7, as shown in FIG. 9. The trunnion 93 and the barrel 15 have a relatively close clearance fit so that the longitudinal axis of the trunnion is rigidly aligned with the axis AX-1 of the barrel. The trunnion 93 may be secured against rotational movement by corresponding flat surfaces inside the prosthesis barrel 15 and on the trunnion, and against axial movement by a set screw 95. A femoral neck finishing tool 97 is then placed on the trunnion 93, and surface 39 of the femoral neck 7 is planed perpendicular to the axis of the barrel AX-1 while even pressure is applied to the finishing tool. Although the seat 39 is shown as being planed by the finishing tool, the seat may have a nonplanar configuration. In that event the finishing tool finishes the seat so that there will be a congruent engagement with the ball assembly collar surface 37. When the collar surface 37 and the seat 39 are congruent, the entire area of the seat engages the collar surface and is subjected to loading by the prosthesis. Loading of the bone material of the seat over the entire area of engagement with the collar surface 37 prevents resorption (withdrawing) of the bone after the prosthesis 1 is implanted. However, although macroscopic congruence is important, microscopic roughness or porosity of the collar surface 37 combined with chemical coating (e.g., calcium phosphate compound) allows an ingrowth of bone from the seat 39 which facilitates bonding of the collar surface with the seat. After finishing, the finishing tool 97 and trunnion 93 are removed.

FIG. 10 illustrates the use of a different finishing tool 99. This tool comprises a finishing wheel 101 (capable of grinding, sanding, cutting or otherwise smoothing and/or shaping) with an integral shaft 103 depending therefrom. The shaft is inserted coaxially with the barrel 15 so that the wheel engages the seat 39. The tool is then rotated on the barrel axis AX-1 to finish seat 39 to the precise shape, smoothness and configuration.

A trial neck-collar-stem assembly (similar to ball assembly 25) is then inserted into the femoral neck and the barrel 15. The collar of this assembly (similar to collar 31) is pulled against the seat 39 of the femoral neck by tightening a set screw (similar to fastener 41). The undersurface of the collar includes a pressure sensor indicator (e.g., pressure sensitive paper) so that the evenness of the load may be determined. If there is an uneven distribution of load on surface 39 of the femoral neck 7, the finishing tool 97 may be used to plane down the high portions causing the uneven distribution.

However, the method of this invention greatly facilitates accurate finishing of the femoral neck 7 to form the seat 39 so that it is substantially perpendicular to the axis of the ball assembly stem 27 and the medial trabecular stream axis AX-5. More specifically, the accuracy is facilitated because the trunnion 93 or shaft 103 of the finishing tool 97 or 99, and the stem 27 of the ball assembly 25 are both coaxially received in the same barrel 15. Because the axis of rotation of the finishing tool precisely coincides with the axis of the stem 27 deviations caused by tolerances of the trunnion, finishing tool and ball assembly stem are minimized. If the finishing tool were guided by structure attached to the outside of the femur otherwise not held in the barrel, the tolerances in the equipment would tend to accumulate causing greater error in planing the femoral neck 7.

Once the seat 39 on the femoral neck 7 is satisfactorily finished, the stem 27 of an appropriate size ball assembly 25 is inserted through the femoral neck coaxially into the barrel 15 to bring the collar surface 37 of the ball assembly into close-fitting, face-to-face engagement with the seat 39 of the femur neck. As may be seen, the method of the present invention greatly facilitates congruent engagement with the collar surface 37. After insertion of the ball assembly stem, fastener 41 is inserted through the sideplate 13 into barrel 15.

The ball 33 of the prosthesis 1 is then placed in the acetabulum (not shown), and the surgically formed opening is closed.

It will be observed from the foregoing that the prosthesis is properly positioned with respect to the femur with a minimum of trial-and-error, and the femur is loaded in a near "normal" way by the prosthesis, thereby reducing the patient's pain and preventing deterioration of the femur after implantation the prosthesis.

In view of the above, it will be seen that the several objects of the invention are achieved and other advantageous results attained.

As various changes could be made in the above constructions and methods without departing from the scope of the invention, it is intended that all matter contained in the above description or shown in the accompanying drawings shall be interpreted as illustrative and not in a limiting sense.

What is claimed is:

1. A method of implanting an extramedullary femoral head-neck prosthesis in a femur, the latter having a shaft and a neck at the upper end of the shaft at the medial side of the femur, comprising:
   determining the axis of the medial trabecular stream of the femur;
   cutting the neck of the femur to form a seat on the femur neck;
   drilling a bore through the shaft of the femur to extend from the neck of the femur down to the lateral side of the shaft along a line substantially parallel to the axis of the medial trabecular stream;
   inserting a barrel having an open end into said bore with the open end of the barrel facing upwardly;
   securing said barrel in fixed position in the bore; and
   inserting a stem of a ball assembly coaxially into said barrel to bring a surface of the ball assembly into congruent, face-to-face engagement with said seat on the femur neck.

2. A method as set forth in claim 1 wherein said step of determining the axis of the medial trabecular stream comprises making a radiological examination of the femur to expose the medial trabecular stream and plotting the average direction of the medial trabecular stream.

3. A method as set forth in claim 1 wherein said barrel has a sideplate at its lower end, said step of securing said barrel in fixed position in said bore comprising fastening said sideplate to the shaft of the femur at the lateral side of the femur.

4. A method as set forth in claim 1 involving the use of a holding device for holding various cutting, drilling and reaming accessories, said holding device having an arm with an outer end, said method further comprising removably securing said holding device to said femoral shaft with the outer end of said arm adjacent the base of the femoral neck.

5. A method as set forth in claim 4 wherein said accessories include a saw guide having a sawcut slot, said step of cutting the neck of the femur comprising operating a saw in the slot of said saw guide to cut the femoral head from the femoral neck and to form said seat.

6. A method as set forth in claim 5 wherein said saw guide is detachably connectable to said arm, said step of cutting the femoral neck further comprising attaching said saw guide to said arm.

7. A method as set forth in claim 4 wherein said holding device includes a tubular guide member having a bore therethrough for guiding a starter drill bit into said femoral shaft at an angle of approximately 90 degrees with respect to the central longitudinal axis of the femoral shaft, said step of drilling a bore through the shaft of the femur comprising inserting a drill bit through said tubular guide member and drilling a relatively short starter hole in the femoral shaft.

8. A method as set forth in claim 4 wherein said holding device includes a guide barrel and a guide sleeve removably receivable in said barrel, said guide sleeve having a bore therethrough for guiding a drill-tipped guide pin into the femoral shaft so that the pin is guided to the center of the femoral neck, said step of drilling a bore through the shaft of the femur further comprising inserting the guide sleeve in said guide barrel, inserting said drill-tipped guide pin in said guide sleeve bore, and drilling a hole in the femoral shaft to the femoral neck.

9. A method as set forth in claim 8 wherein said accessories include an accessory adapted to be attached to said arm, said accessory comprising a member having an opening therein generally in alignment with the central longitudinal axis of said sleeve whereby the position of the holding device with respect to the center of the femoral neck may be checked to determine the position of said drill-tipped guide pin with respect to the femoral neck, said step of drilling a bore through the shaft of the femur comprising attaching said accessory to said arm, centering said opening with respect to the cut surface of the femoral neck and running said guide pin through said guide sleeve bore and the femur.

10. A method as set forth in claim 9 involving the use of a reamer adapted slideably to pass through said guide barrel, said reamer having a central bore coaxial with the reamer for guiding the reamer on said guide pin, said method further comprises running said reamer along said guide pin through the shaft of the femur to form said bore for receiving said prosthesis barrel.

11. A method as set forth in claim 1 involving the use of a trunnion and a finishing tool, said method further comprising inserting said trunnion coaxially into said prosthesis barrel so that it projects partially through said seat of the femoral neck, securing the trunnion against rotational and axial movement relative to said barrel, placing said finishing tool on said trunnion, and rotating the finishing tool to finish said seat.

12. A method as set forth in claim 1 wherein the finishing tool includes a finishing wheel and a shaft depending therefrom, the step of rotating the finishing tool on the axis of the barrel comprising inserting the shaft of the finishing tool coaxially into said prosthesis barrel so that the finishing wheel engages said seat, and rotating the finishing tool shaft in said barrel to finish said seat.

* * * * *